US008338129B2

(12) United States Patent
Bernardi et al.

(10) Patent No.: US 8,338,129 B2
(45) Date of Patent: Dec. 25, 2012

(54) METHOD FOR READING IMAGES, IN PARTICULAR FOR STUDYING THE DEVELOPMENT OF BIOFILM IN A CULTURE MEDIUM

(75) Inventors: Thierry Bernardi, Perignat-les-Sarlieve (FR); Nicolas Bara, Paris (FR)

(73) Assignee: Biofilm Control (FR)

( * ) Notice: Subject to any disclaimer, the term of this patent is extended or adjusted under 35 U.S.C. 154(b) by 1012 days.

(21) Appl. No.: 12/282,364

(22) PCT Filed: Mar. 8, 2007

(86) PCT No.: PCT/FR2007/050891
§ 371 (c)(1),
(2), (4) Date: Dec. 22, 2008

(87) PCT Pub. No.: WO2007/104881
PCT Pub. Date: Sep. 20, 2007

(65) Prior Publication Data
US 2009/0233328 A1    Sep. 17, 2009

(30) Foreign Application Priority Data
Mar. 10, 2006  (FR) ...................................... 06 02145

(51) Int. Cl.
*C12Q 1/04*      (2006.01)
*C12N 5/00*      (2006.01)

(52) U.S. Cl. .......................................... 435/34; 435/325
(58) Field of Classification Search ....................... None
See application file for complete search history.

(56) References Cited

U.S. PATENT DOCUMENTS

| 3,635,678 A | 1/1972 | Seitz et al. |
| 6,441,894 B1 | 8/2002 | Manian et al. |
| 7,955,818 B2 * | 6/2011 | Bernardi et al. ................ 435/34 |
| 2001/0033414 A1 | 10/2001 | Yahiro |

FOREIGN PATENT DOCUMENTS

| EP | 0 323 322 A1 | 7/1989 |
| WO | 97/12678 A1 | 4/1997 |
| WO | 01/86255 A | 11/2001 |
| WO | 03/095995 A1 | 11/2003 |
| WO | 2005/090944 A1 | 9/2005 |

OTHER PUBLICATIONS

J. W. Costerton et al. "Bacterial Biofilms: A Common Cause of Persistent Infections", 1999, *Science*, vol. 284, pp. 1318-1322.

* cited by examiner

*Primary Examiner* — Jehanne Sitton
(74) *Attorney, Agent, or Firm* — DLA Piper LLP (US)

(57) ABSTRACT

A method for reading images of a base of a plate provided with at least one well containing a culture medium of microorganisms includes: i) forming a opaquing layer covering a surface of the culture medium to form a reading base; and ii) imaging, at specific time intervals, the base of the well using an imaging optical device.

9 Claims, 1 Drawing Sheet

METHOD FOR READING IMAGES, IN PARTICULAR FOR STUDYING THE DEVELOPMENT OF BIOFILM IN A CULTURE MEDIUM

RELATED APPLICATIONS

This application is a §371 of International Application No. PCT/FR2007/050891, with an international filing date of Mar. 8, 2007 (WO 2007/104881 A2, published Sep. 20, 2007), which claims priority of French Patent Application No. 06/02145, filed Mar. 3, 2006, the subject matter of which is incorporated by reference.

TECHNICAL FIELD

This disclosure relates to the field of the study of the behavior of micro-organism cultures.

The disclosure more particularly, but not exclusively, relates to the field of the study of the development of a biofilm in a homogeneous or non-homogeneous culture medium.

The expression "culture medium" means any medium wherein at least one micro-organism is liable to be present and to develop. Thus, it is a medium which can be natural or synthetic. Thus, water falls within this definition, for example. "Culture medium" thus means the micro-organism and the medium wherein it can be found, or possibly the medium alone.

BACKGROUND

Biofilms are formed of various layers of bacteria or micro-organisms, contained in a solid matrix. They develop to form microbian communities, one of the properties of which consists in adhering to submerged surfaces. Such adhesion is either not specific (adherence), or specific (adhesion proper) (Costerlon et al. Bacterial Biofilms, Sciences 1999; 284-6):

Adherence or reversible adhesion: Existing micro-organisms get closer to the surfaces by gravitation, Brownian motions or chimiotactism if they have flagella. During this first step of fixation which calls for only two purely physical phenomena and weak physicochemical interactions, micro-organisms can still be easily detached.

Adhesion: This slower step calls for stronger interactions as well as the microbian metabolism and the cellular appendices of the micro-organism (flagella, pilis, . . . ). The adhesion is an active and specific phenomenon. Some first pioneers are going to fix in an irreversible way to the surface more particularly thanks to the synthesis of exopolysaccharids (EPS). This process is relatively slow and depends on the present environmental factors and micro-organisms.

Such biofilms can be found everywhere in numerous fields, wherein they entail health hazards and may cause relatively important damages.

As regards the health of human beings, for example, biofilms are responsible for infections which are more and more difficult to contain: on the whole nose-ear-throat area (auditory canal, mucous membrane of nose and sinus, eye conjunctiva . . . ), on teeth (occurrence of tartar, decays, . . . ), on bronchus, lungs (in patients suffering from mucoviscidosis . . . ), at the level of the urinary genital tract etc ( . . . ). In addition, they are the origin of most nosocomial pathologies (over 10,000 diseases per year) by forming at the level of catheters or implants (heart valves, artificial hips, urinary catheters . . . ) (J. W. Costerton, P. Stewart and E. P. Greenberg, Bacterial Biofilms: "A common cause of persistent infections". Science, Vol. 284, pages 1318-1322).

Biofilms also concern the farm and food industry as regards their implication in food poisonings (formation upon the breaking of the cold chain, development on cutting tools, grinding tools, or on workbenches). They are also present in cooling towers and responsible for infections by the Legionelles.

The development and behavior of such biofilms remain poorly known, however, because studying them is complex, although many methods for studying the development of biofilms have been implemented.

Among the methods implemented to study the behavior of such microbian communities, the one described in WO 2005/090944 is known. That method is based on modelling the development of biofilms in a non-homogeneous, cloudy and opaque medium corresponding to the culture medium wherein micro-organisms develop to form such biofilms.

Such modelling is carried out from the measurement of the viscosity of the culture medium. The notion of viscosity only partially describes the effect of the biofilm. The biofilm is composed of:

on the one hand, a certain quantity of exopolysaccharids (EPS), or any other viscous substance, produced by micro-organisms, and on the other hand, through a network, a meshing, of fibers and cellular bodies. Micro-organisms use cellular appendices from the micro-organism (flagella, pilis . . . ) to adhere onto the surfaces.

The measure more specifically corresponds to a measure of viscosity and a measure of resistance to traction on cellular appendices. The measurement uses magnetizable, magnetic or electrically loaded particles (or balls) (which can be magnetized or electrically loaded under the effect of a magnetic, electromagnetic or electric field), or covered with at least one magnetic or magnetizable layer. In the following text, the term "magnetic" refers to the expression "electrically loaded" or to the terms "magnetic" or "magnetizable" or to the expression "covered with at least one magnetic or magnetizable layer," indifferently. Such particles which exist on the surface where the biofilm is going to develop will be trapped by the viscous substance delivered by the microorganisms and by the cellular appendices used by the micro-organisms. The particles are immobilized by the two factors, in variable proportions/ratios depending on the studied micro-organisms.

Thus, the method described in the above-mentioned application consists in:

immerging at least one magnetic particle into a culture medium wherein the culture medium is preferably positioned in one or several well(s) of a micro-plate, submitting the culture medium to a magnetic, electric or electromagnetic field, so that the particle is moved, detecting the degree of motion freedom of the particle in the culture.

The degree of mobility of particles is reduced or null if the viscosity increases, further to the production of EPS by the micro-organisms, or if the micro-organisms develop cellular appendices (flagella, pilis . . . ) to adhere to a surface, thus trapping the particles at the same time.

This last step c) is preferably carried out by means of an optical measurement. It deals with the lighting of the base of the wells in the micro-plate using a light source, so as to light the magnetic particle(s), and thus to determine the motion of the particle(s) in the culture medium, by comparing images. Such comparison is carried out, on the one hand, prior to and after the effect of a magnetic, electric or electromagnetic field, and on the other hand, at given time intervals (a time for micro-organism to develop and form a biofilm or not).

The optical detection devices used are conventional imaging devices (scanner, still camera or film camera). The views correspond to the base of the well, as seen from under, by transparency. The conventional optical path successively goes through the following elements:
- external base of the well,
- materials composing the base of the well (transparent: plastic, glass . . . ),
- internal base of the well,
- culture medium,
- culture medium meniscus,
- air above the culture medium.

Whatever the imaging system, the experiment operator faces a major problem related to the formation of reflections between the base of the well and the liquid surface of the culture medium because of the existence of a meniscus in the culture medium. The image obtained by the optical detection device is thus particularly complex, or even sometimes impossible to process.

In addition to the difficulties in analyzing the image relating to the meniscus formed on the surface of the culture medium, the experiment operator also has to face a problem relating to the parallax between the image of the wells disposed at the center of the micro-plate, and the image of the wells disposed at the edge of the micro-plate, when he/she wishes to read simultaneously the images corresponding to each well of the micro-plate. If the base at the central well can easily be distinguished, this is not true for the base of the well at the periphery of the micro-plate. The image obtained is in fact altered by the image of the wall of the well (lower face and upper face), and the shift between the base of the well, the surface of the meniscus formed by the liquid contained in the well, and the upper opening of the well. Such air-plastic (or glass or any other transparent material), plastic (or glass or any other transparent material), culture medium, culture medium-air dioptres, create a composite image which is all the more complex as the parallax is important, as the source of reflections, more particularly, on the wall of the well.

SUMMARY

We provide a method for reading images of a base of a plate provided with at least one well containing a culture medium of micro-organisms including forming an opaquing layer covering a surface of the culture medium to form a reading base, and imaging, at specific time intervals, the base of the well using an imaging optical device.

We also provide a plate that implements registering the base of the wells of the method, including a plurality of wells that receive samples of a culture medium of microorganisms, the base of the wells including registering means making it possible to register a periphery of the base of the well.

BRIEF DESCRIPTION OF THE DRAWINGS

Other objects and advantages will appear upon reading the following description, and while referring to the appended drawings, wherein.

DETAILED DESCRIPTION

Figure 1:
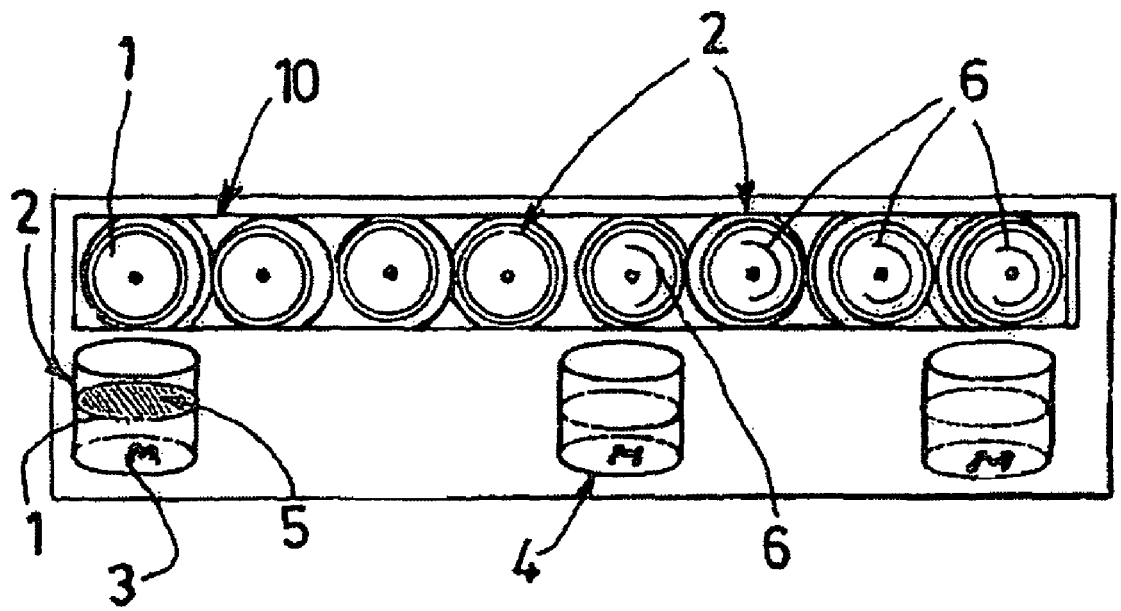
FIG. 1 illustrates wells containing a culture medium which is covered or not with an opaquing layer and the corresponding image obtained from the base of the wells.

We address the difficulties met by the experiment operator during the analysis of the images of the base of the well by providing a method for reading images at the base of wells, and adapted equipment, to make it possible to eliminate the effect of the meniscus, or at least to limit the interference thereof.

For this purpose and according to a first aspect, we provide a method for reading images of the base of a plate provided with at least one well containing a culture medium for microorganisms, including the following steps:
i) forming an opaquing layer covering the surface of the culture medium so as to form a base for reading, and
ii) imaging the base of the well using an optical imaging device at predetermined intervals of time.

The word "base" means the low wall of the well, the face of the concerned wall being indifferently the inner face or the outer face. The particles seen are on the upper face side (at the base of the well).

Within the scope of the study of the development of a biofilm in the culture medium, the step of imaging comprises a first imaging of the base of the well corresponding to a reference image, and at least a second imaging following the application of a magnetic, electric or electromagnetic field on the culture medium, the medium containing at least one particle which is magnetic, magnetizable, electrically loaded or covered with at least one magnetic or magnetizable layer.

Preferably, the opaquing layer is obtained by the deposition into the well of a composition which is not miscible with the culture medium.

Thus, thanks to the deposition of an opaquing product which is not miscible with the culture medium at the surface of the medium, the reflections between the base of the wells and the surface of the liquid are eliminated, the reading of images being improved as regards clarity.

Advantageously, the opaquing layer is obtained by deposition into the well of a composition having a density lower than that of the culture medium, to remain at the surface of the culture medium.

In addition, to optimize the image clarity, the opaquing layer will be made to form, at the surface of the culture medium, a homogenous layer which is uniformly distributed.

The opaquing layer formed will be advantageously opaque and non reflecting, to eliminate the "mirror" effect of the meniscus.

Similarly, to prevent any physical and/or chemical interaction with the culture medium, the composition composing the opaquing layer will advantageously be inert. Similarly, with respect for the operator, it will be preferable to use a non toxic composition.

Advantageously, the opaquing layer comprises translucent oil containing a miscible pigment or water repellent microparticles.

According to a preferred aspect, the method will further comprise, with the view to analyzing the images read, a previous step of registering the base of the well so as to retrieve images taken by the optic device from the images of the wall of the well, and thus analyze the images of the base of the well only. This previous registering of the base of the well thus makes it possible to solve the problem related to the parallax between the image of the wells at the center of the micro-plate, and the image of the wells at the edge of the micro-plate.

According to a second aspect, a plate comprising comprises a plurality of wells intended to receive samples from a culture medium of micro-organisms, characterised in such that the base of the wells includes registering means making it possible to register the periphery of the base of said the well.

Preferably, the registering means consist of a plurality of marks located at the base of the wells and positioned as an extension of the outside walls of the wells.

The formation of registrations, and in particular marks, as cavities or reliefs, at the base of well, and on the extension of the side walls of the well, allows a better registering of the base of the wells, and thus the solution to the problem connected to the parallax between the image of the wells at the center of the micro-plate, and the image of the wells at the edge of the micro-plate.

Advantageously, the base of the wells comprises three marks distributed along a 120 degree angle.

The wells are provided with a transparent base to enable imaging through the base.

Figure 2:
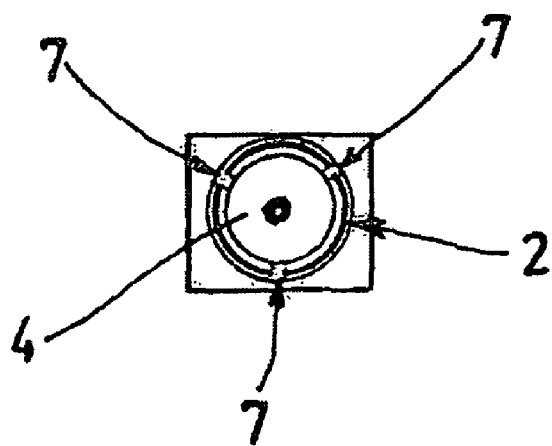
FIG. 2 is a view of the base of a well.

As regards FIGS. 1 and 2, equipment and a method making it possible to image a culture medium 1 and will act their analysis with the view to studying the development of a biofilm in the medium 1, are described.

For this purpose, the equipment includes a micro-plate 10 comprising wells 2 wherein the culture medium 1 is positioned. In the illustrated example, the micro-plate 10 includes eight aligned wells 2.

Magnetic balls 3 are positioned at the base of each well 2. Such magnetic balls aim at making it possible to measure the viscosity of the culture medium by measuring the degree of freedom of balls. As a matter of fact, depending on the degree of the development of the microorganisms, the motion of the magnetic balls under the effect of a magnetic, electric or electromagnetic field will be more or less hindered by the biofilm. Starting from the measurements of the viscosity of the culture medium at given time intervals, the modelling of the development and the behavior of the biofilm existing in the culture medium 1 will be performed. Such measurement is preferably carried out by comparing an image of the base of the well prior to the effect of the magnetic, electric or electromagnetic field, and an image after such an effect.

To enable the imaging by an optical device, of the scanner type, the wells 2 advantageously have a transparent base 4.

As biofilms mainly develop in an aqueous environment, and adhere to submerged surfaces, i.e., magnetic balls 3, the selected culture medium 1, in the illustrated example, is water.

To eliminate the reflections between the base of the wells 2 and the surface of the culture medium 1, which interferes with the reading and the interpretation of the images, a layer on the reading base 5 is positioned at the surface of the culture medium 1.

This reading base layer 5 is composed of a composition which is non-miscible with water, the culture medium 1 being aqueous and having a density which is lower than that of the culture medium 1. Thus, the reading base layer 5 remains i) perfectly separated from the culture medium 1, and ii) above the meniscus, thus creating an opaquing image base.

Preferably, a white composition will be chosen, such as an "oil pigment" diluted into oil, or a composition the color of which is in contrast with the color which is to be detected in the wells 2.

Besides, the composition selected will preferably be chemically and physically inert with respect to the culture medium 1, and non-toxic to make its handling easier.

Besides, the composition placed at the surface of the culture medium 1 should preferably be composed of a non-reflecting opaque layer, to eliminate the "mirror" effect of the meniscus.

Preferably but not exclusively, the composition includes a translucent oil containing a miscible colorant, without any partition coefficient with water, or a translucent oil mixed with water repellent microparticles, such as micronized Téflon®.

Although the implementation thereof is more difficult, water repellent powders or waxes can also be used to make the opaquing layer.

The reading base layer 5, thus composed and formed at the surface of the culture medium 1, makes it possible to eliminate the reflections formed by the surface of the culture medium 1.

When the composition is deposited into the well 2 and a preferably uniform opaquing layer (without any excessive thickness) covering the whole surface of the medium 1, is formed at the surface of the culture medium 1, the micro-plate 10 is positioned above a scanner intended to image the base of the wells 2 for the first time (reference image), then a plurality of images are taken, at given time intervals, after the application of a magnetic, electric or electromagnetic field for a given time (of the order of one minute for example) according to the principle described in WO 2005/090944. By comparing the images with image analyzing software, it is possible to estimate the degree of immobilization of the particles. If the particles are movable (without the presence of micro-organisms for example), they form an opaque mass at the point of the maximum intensity of the magnetic (or electric or electromagnetic) field. If the particles are immobilized, no difference between both images can be seen. Depending on the evolution of the development of the biofilm, an evolution of the difference between both images can be observed.

In FIG. 1, the images of the base 4 of the wells read by the scanner are illustrated, with the four leftmost wells 2 containing a culture medium 1 covered by a reading base layer 5, the four rightmost wells 2 containing a culture medium 1 without any reading base layer.

The image of the base 4 of the four rightmost wells 2 clearly shows the presence of the meniscus 6 which makes the interpretation of the image more difficult, whereas no meniscus appears when the wells have a reading base layer 5 (refer to the four leftmost wells).

The interpretation of one image when the well has no reading base layer 5 is all the more difficult as the problem related to the parallax effect which is maximum at the edge of the micro-plate, is added to the problem of the presence of the meniscus.

Thus, to remedy this last problem, wells 2 will advantageously be provided, the bases 4 of which have marks 7, as an extension of the side walls (refer to FIG. 2).

According to a preferred, the base 4 of the wells 2 comprises three marks spaced from each other along a 120 degree angle, to clearly define the base 4 of the wells 2.

Advantageously, the marks 7 are pyramid-shaped holes.

The structures and methods described herein are given as examples. It should be understood that those skilled in the art may make various modifications without departing from the scope of this disclosure.

The invention claimed is:

1. A method for reading images of a base of a plate provided with at least one well containing a culture medium of micro-organisms comprising:
   i) forming an opaquing layer covering a surface of the culture medium to form a reading base, and
   ii) imaging, at specific time intervals, the base of the well using an imaging optical device, comprising a first imaging of the base of the well corresponding to a reference image, then at least one second imaging after application of a magnetic, electric or electromagnetic field on the culture medium, the medium containing at least one particle which is magnetic, magnetizable, electrically loaded or covered with at least one magnetic or magnetizable layer.

2. The method according to claim 1, wherein the opaquing layer is made by deposition into the well of a composition not miscible with the culture medium.

3. The method according to claim 1, wherein the opaquing layer is made by deposition into the well of a composition having a density lower than that of the culture medium.

4. The method according to claim 1, wherein the opaquing layer is made to form at the surface of the culture medium a homogeneous and uniformly distributed layer.

5. The method according to claim 1, wherein the opaquing layer formed is a non-reflecting opaque layer.

6. The method according to claim 1, wherein the opaquing layer formed is inert.

7. The method according to claim 1, wherein the base of the well is registered to analyze the images read so that only images corresponding to the base of the well are analyzed.

8. A method for reading images of a base of a plate provided with at least one well containing a culture medium of micro-organisms comprising:
   i) forming an opaquing layer comprising a translucent mineral oil containing a miscible pigment that covers a surface of the culture medium to form a reading base, and
   ii) imaging, at specific time intervals, the base of the well using an imaging optical device.

9. A method for reading images of a base of a plate provided with at least one well containing a culture medium of micro-organisms comprising:
   i) forming an opaquing layer comprising a translucent oil containing water-repellent microparticles that covers a surface of the culture medium to form a reading base, and
   ii) imaging, at specific time intervals, the base of the well using an imaging optical device.

* * * * *